(12) United States Patent
Ali et al.

(10) Patent No.: US 9,872,956 B2
(45) Date of Patent: Jan. 23, 2018

(54) LIMITING PRESSURE IN AN IMPLANTED CATHETER

(75) Inventors: Irfan Z. Ali, Woodbury, MN (US); Scott L. Kalpin, Harris, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 2004 days.

(21) Appl. No.: 13/097,316

(22) Filed: Apr. 29, 2011

(65) Prior Publication Data

US 2012/0277717 A1 Nov. 1, 2012

(51) Int. Cl.
*A61M 5/168* (2006.01)
*A61M 5/142* (2006.01)

(52) U.S. Cl.
CPC .... *A61M 5/16804* (2013.01); *A61M 5/14276* (2013.01); *A61M 5/16854* (2013.01); *A61M 5/16877* (2013.01)

(58) Field of Classification Search
CPC .......... A61M 5/16804; A61M 5/14276; A61M 5/16854; A61M 5/16877
USPC ........... 604/65, 67, 151, 500, 502, 506–508, 604/890.1
See application file for complete search history.

(56) References Cited

U.S. PATENT DOCUMENTS

| | | | |
|---|---|---|---|
| 4,530,696 A | 7/1985 | Bisera | |
| 4,985,015 A | 1/1991 | Obermann | |
| 5,024,668 A | 6/1991 | Peters | |
| 5,040,536 A | 8/1991 | Riff | |
| 5,560,366 A | 10/1996 | Harada | |
| 5,645,531 A * | 7/1997 | Thompson et al. | ............ 604/67 |
| 6,364,842 B1 | 4/2002 | Amano | |
| 7,338,464 B2 | 3/2008 | Blischak | |
| 7,505,869 B2 | 3/2009 | Hartlaub | |
| 7,621,878 B2 | 11/2009 | Ericson | |
| 2002/0065471 A1 | 5/2002 | Amano | |
| 2004/0230125 A1 | 11/2004 | Amano | |
| 2005/0075624 A1 | 4/2005 | Miesel | |
| 2005/0090799 A1 * | 4/2005 | Morris | ......................... 604/500 |
| 2005/0148885 A1 | 7/2005 | Tweed | |
| 2005/0222643 A1 | 10/2005 | Heruth | |
| 2005/0241387 A1 | 11/2005 | Miesel | |
| 2006/0060190 A1 | 3/2006 | Sinderby | |
| 2006/0079793 A1 | 4/2006 | Mann | |
| 2007/0232936 A1 | 10/2007 | Mann | |

(Continued)

*Primary Examiner* — Kevin C Sirmons
*Assistant Examiner* — Amber Stiles
(74) *Attorney, Agent, or Firm* — Mueting, Raasch & Gebhardt, P.A.

(57) ABSTRACT

A method includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate and monitoring pressure via a pressure sensor in communication with the lumen of the catheter. Monitoring the pressure includes acquiring pressure data from the pressure sensor at a first frequency. The method also includes (i) determining whether the monitored pressure exceeds a first threshold, wherein the first threshold is based on the data regarding the catheter; and (ii) decreasing the rate at which the fluid is delivered from the reservoir into the catheter if the monitored pressure is determined to exceed the threshold.

21 Claims, 12 Drawing Sheets

(56) References Cited

U.S. PATENT DOCUMENTS

2007/0258083 A1    11/2007  Heppell
2010/0016918 A1      1/2010  Mann
2010/0259406 A1*  10/2010  Caso et al. ................. 340/686.6
2011/0295191 A1*  12/2011  Injev ................... A61F 9/00745
                                                           604/22

* cited by examiner

LIMITING PRESSURE IN AN IMPLANTED CATHETER

FIELD

The present disclosure relates generally to devices, systems and methods for limiting pressure in implanted catheters, such as catheters operably coupled to implantable infusion devices.

BACKGROUND

Implantable infusions systems have been used to treat a variety of diseases, such as spasticity, pain and cancer by targeting drug delivery to a selected area of a patient. Therapies employing such systems have proven to be very helpful for patients for whom systemic therapy is not effective, possible, or practicable. The implantable systems typically include an implantable infusion device containing a reservoir for housing the drug and a catheter coupled to the reservoir to direct the drug to the target area. The devices typically include a pump or mechanism for driving fluid from the reservoir, or withdrawing fluid from the reservoir, and through the catheter to the selected area of the patient.

A variety of catheters have been used or proposed for use in implantable infusion systems. Each type of catheter has unique properties, such as compliance and resistance to bursting under pressure. While not common, implanted catheters that are operably coupled to implantable infusion devices may become occluded. Because each type of catheter has a different resistance to bursting, often only more robust and less compliant catheters are used so that the possibility of rupturing is reduced or eliminated. However, it may be desirable to use less robust or more compliant catheters in some situations; as such catheters may be softer or thinner and may cause less damage to tissue when implanted.

SUMMARY

This disclosure, among other things, describes devices, systems and methods for monitoring pressure with a catheter during use and limiting the pressure by controlling the rate of delivery of therapeutic agent via an infusion device. By monitoring and limiting pressure within the catheter during use, less robust catheters may be employed. Of course the methods, systems and devices described herein may be employed with more robust catheters as well.

In various embodiments described herein, a method carried out by an implantable infusion device includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate and monitoring pressure via a pressure sensor in communication with the lumen of the catheter. Monitoring the pressure includes acquiring pressure data from the pressure sensor at a first frequency. The method also includes (i) determining whether the monitored pressure exceeds a first threshold, wherein the first threshold is based on the data regarding the catheter; and (ii) decreasing the rate at which the fluid is delivered from the reservoir into the catheter if the monitored pressure is determined to exceed the threshold.

In some embodiments described herein, a method carried out by an implantable infusion device. The method includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate, and monitoring pressure via a pressure sensor in communication with the lumen of the catheter. Monitoring the pressure includes acquiring pressure data from the pressure sensor at a first frequency. The method also includes determining whether the monitored pressure exceeds a first threshold. The first threshold is based on the data regarding the catheter. The method additionally includes (i) monitoring a rate of infusion of fluid from the reservoir into the lumen of the catheter; (ii) determining whether the rate of infusion exceeds a threshold rate of infusion; and (iii) increasing the frequency of acquisition of pressure data from the pressure sensor if the monitored pressure is determined to exceed the first threshold or if the monitored rate of infusion is determined to exceed the threshold rate of infusion.

In numerous embodiments described herein, a method carried out by an implantable infusion device. The method includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate and monitoring pressure via a pressure sensor in communication with the lumen of the catheter. Monitoring the pressure includes acquiring pressure data from the pressure sensor at a first frequency. The method also includes (i) monitoring a rate of infusion of fluid from the reservoir into the lumen of the catheter; (ii) deriving a threshold pressure based on the data regarding the catheter and the monitored rate of infusion; (iii) determining whether the pressure exceeds the threshold; and (iv) increasing the frequency of acquisition of pressure data from the pressure sensor if the monitored pressure is determined to exceed the threshold.

In embodiments, a method carried out by an implantable infusion device includes (i) receiving data regarding a catheter being used with the infusion device, the catheter having a lumen operably coupled to a reservoir of the infusion device and configured to deliver fluid from the infusion device to a target location of a patient; (ii) infusing fluid from the reservoir into the lumen of the catheter at a first rate; (iii) monitoring pressure via a pressure sensor in communication with the lumen of the catheter, wherein monitoring the pressure comprises acquiring pressure data from the pressure sensor at a first frequency; (iv) determining whether the monitored pressure exceeds a first threshold, wherein the first threshold is based on the data regarding the catheter; and (v) increasing the frequency of acquisition of pressure data from the pressure sensor if the monitored pressure is determined to exceed the first threshold.

In embodiments, a method carried out by an implantable infusion device includes (i) monitoring pressure via a pressure sensor in communication with the lumen of a catheter, wherein monitoring the pressure comprises acquiring pressure data from the pressure sensor at a first frequency; (ii) determining whether the monitored pressure exceeds a threshold; and (iii) increasing the frequency of acquisition of pressure data from the pressure sensor if the monitored pressure is determined to exceed the threshold.

In embodiments, a method carried out by an implantable infusion device includes (i) infusing fluid from a reservoir into a lumen of a catheter at a first rate; (ii) monitoring pressure via a pressure sensor in communication with the lumen of the catheter, wherein monitoring the pressure comprises acquiring pressure data from the pressure sensor at a first frequency; (iii) determining whether the monitored pressure exceeds a first threshold; (iv) monitoring a rate of infusion of fluid from the reservoir into the lumen of the catheter; (v) determining whether the rate of infusion exceeds a threshold rate of infusion; and (vi) increasing the frequency of acquisition of pressure data from the pressure sensor if the monitored pressure is determined to exceed the first threshold or if the monitored rate of infusion is determined to exceed the threshold rate of infusion.

In embodiments, a method carried out by an implantable infusion device includes (i) infusing fluid from a reservoir into a lumen of a catheter at a first rate; (ii) monitoring pressure via a pressure sensor in communication with the lumen of the catheter, wherein monitoring the pressure comprises acquiring pressure data from the pressure sensor at a first frequency; (iii) monitoring a rate of infusion of fluid from the reservoir into the lumen of the catheter; (iv) determining whether the rate of infusion exceeds a threshold rate of infusion; and (v) increasing the frequency of acquisition of pressure data from the pressure sensor if the monitored rate of infusion is determined to exceed the threshold rate of infusion Computer readable media and implantable infusion devices configured to carry out the methods described above are discussed and contemplated herein.

One or more embodiments of the systems, devices and methods described herein may provide one or more advantages over prior systems, devices and methods for detecting catheter complications by sensing pressure within the catheter. Such advantages will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

This disclosure, among other things, describes devices, systems and methods for monitoring pressure with a catheter during use and limiting the pressure by controlling the rate of delivery of therapeutic agent via an infusion device. By monitoring and limiting pressure within the catheter during use, a variety of catheters with varying degrees of robustness may be employed. The devices, systems and methods described herein may be used to reduce the likelihood that a less robust catheter will burst when occluded.

Figure 1:
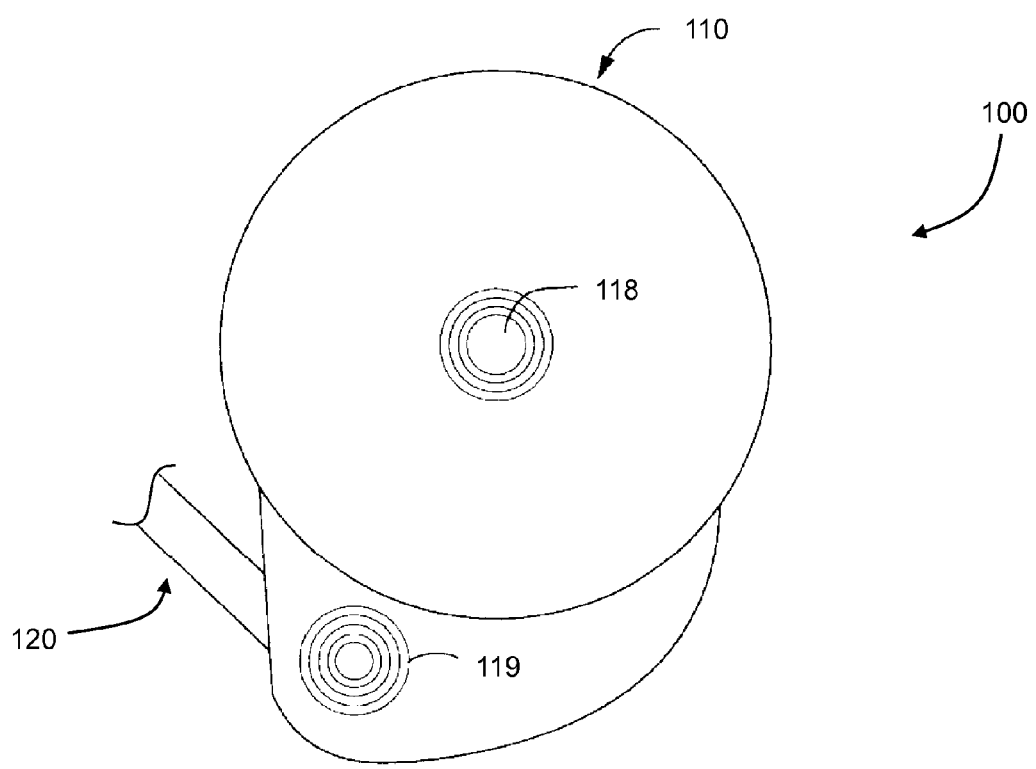
FIG. 1 is a schematic top view of an implantable infusion system that includes an implantable infusion device and a catheter.
Figure 2:
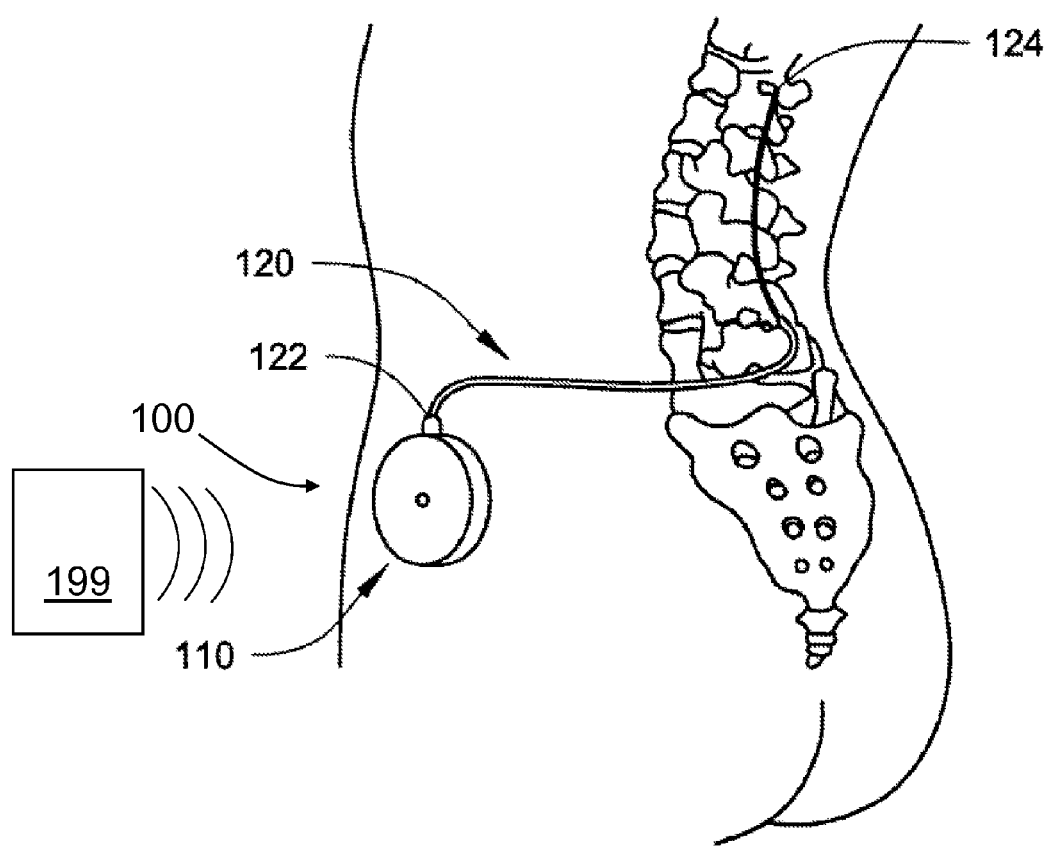
FIG. 2 is a schematic view showing an implatable infusion system implanted in a patient.

The devices, methods and systems described herein may be employed with any suitable implantable infusion system. FIGS. 1-2 show examples of infusion systems 100 that may be used in accordance with the teachings presented herein. The infusion system depicted in FIG. 1 includes an infusion device 110, a catheter 120, and a catheter access port 119 in fluid communication with the catheter 120. The infusion device 110 also includes a refill port 118 in communication with a reservoir (note shown in FIG. 1) for containing a fluid therapeutic substance disposed within the housing of the device 110. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, etc.), or the like. Examples of some potentially suitable infusion devices may include, e.g., commercially available implantable infusion pumps such as, for example, the SYNCHROMED II and EL pumps, manufactured by Medtronic, Inc., Minneapolis, Minn.

The infusion system 100 depicted in FIG. 2 is shown implanted in a patient. The infusion system 100 includes an infusion device 110 and catheter 120 having a proximal end 122 attached to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 2, the cerebroventricles, or elsewhere as desired). While not shown in FIG. 2, it will be understood that the depicted infusion device 110 may include a catheter access port in fluid communication with the catheter 120 as described above with regard to FIG. 1. The infusion device 110 may also include a reservoir that contains a fluid (e.g., a therapeutic substance) to be infused using the system. The fluid contained within the reservoir may preferably be replenished periodically using known techniques and structures.

It will be understood that the catheter and system depicted in FIG. 2 is for purposes of example and not limitation. Any suitable infusion device may be employed. In addition, the catheter may be of any length, diameter, etc. In embodiments, the catheter is a separate unit that is attached to an outlet port of the infusion device. In embodiments, the catheter is the outlet port of the infusion device.

As shown in FIG. 2, an external device 199 such as a programmer device, a computer, a personal data assistant, or the like, may wirelessly communicate with the infusion device 110 to provide operating instructions or information regarding the catheter 120 being used in combination with the infusion device 110. In some embodiments, a chip or circuit may be embedded in or on the proximal end 122 of the catheter and readable by the infusion device 110 so that the infusion device is informed with regard to the particular catheter being employed.

Figure 3:
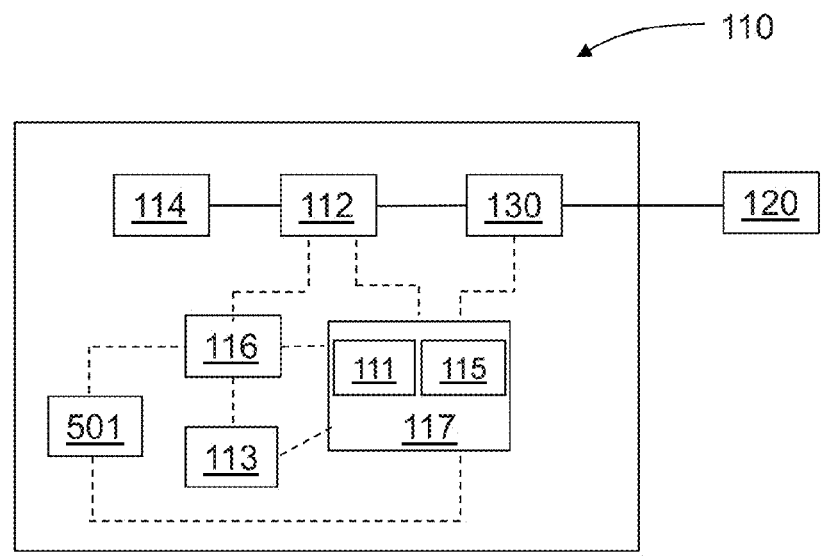
FIG. 3 is a schematic block diagram showing some selected components of an implantable infusion device, where dashed lines represent electrical connections and solid lines represent fluid connections.

An overview of selected components of an example of an implantable infusion device 110 is depicted in FIG. 3. The depicted infusion device 110 includes a pump mechanism 112 operably coupled to a catheter 120 such that fluid within a reservoir 114 can be delivered to the catheter 120 via the pump mechanism 112. The depicted infusion device 110 includes a power supply 116 and control electronics 117 operably coupled to the power supply 116 and the pump mechanism 112 such that the infusion of fluids using the system can be controlled. The control electronics 117 may include a processor 115 and memory 111, such as RAM or ROM. Although not specifically depicted, the infusion device may also include other components typically or desirably included in an implantable infusion device.

The implantable infusion device 110 depicted in FIG. 3 also includes a pressure sensor 130 that is operably coupled to the control electronics 117. The pressure sensor 130 is operably coupled to the catheter 120 in a manner that allows the pressure sensor 130 to measure the pressure of fluid located within the lumen of the catheter 120 and to provide a pressure signal (to, e.g., the control electronics 117) that is representative of the fluid pressure of the fluid in the catheter 120.

The infusion device 110 may also include a communication circuit and components 501, such as a telemetry antenna, for communication with another device, such as an external programmer device 199, for receiving operating instructions, receiving information regarding the catheter being used in connection with the infusion device, for transmitting information regarding catheter occlusion status, or the like. The device 110 may also include an indicator circuit and components 113, such as an audible alarm or vibration mechanism, operably coupled to the power supply 116 and the control electronics 113 for providing an alert or sensory cue to the patient when an occluded catheter condition is detected.

Figure 4:
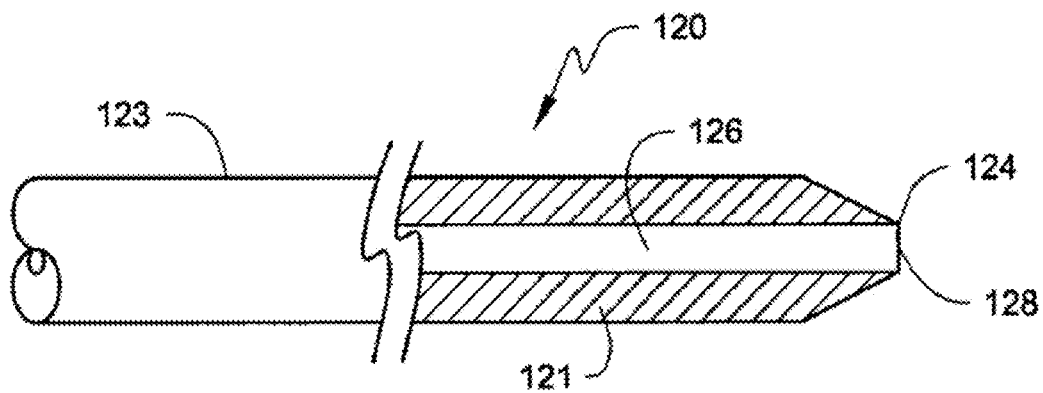
FIG. 4 is a partial sectional view of a portion of a catheter.

FIG. 4 depicts a portion of a catheter 120 in an enlarged cross-sectional view. The catheter 120 includes an elongated tubular portion 123 that preferably extends from the proximal end (not shown) to the distal end 124. The catheter 120 depicted in FIG. 4 includes a lumen 126 that terminates at opening 128 (or delivery region) at the distal end 124. Therapeutic substances (or other fluids) delivered from the infusion device 110 to the catheter 120 pass through lumen 126 and preferably exit the catheter 120 through opening 128 (also referred to herein as "delivery region" or "infusion section").

The body 121 of catheter 120 may be constructed of any suitable material, e.g., an elastomeric tube. Examples of some suitable materials include, but are not limited to, silicone rubber (e.g., polydimethyl siloxane) or polyurethane, both of which can provide good mechanical properties and are very flexible. Suitable materials for the catheter 120 are also preferably chemically inert such that they will not interact with therapeutic substances, body tissues, or body fluids while implanted in the patient.

Although the opening 128 through which the fluid exits the catheter 120 is depicted as a simple opening in the distal end 124 of catheter 120, such an opening 128 is only one embodiment of an infusion section that may be used in connection with the teachings presented herein. Other embodiments of infusion sections may include, e.g., multiple openings, permeable membranes, or the like. Although the infusion section (opening 128) of the depicted catheter 120 is located at the distal end 124 of the catheter 120, the infusion section(s) may be positioned at any location along the length of the catheter 120 that can be used to deliver the fluid to the selected internal delivery site. In some embodiments, the catheter serves as an exit port of an infusion device or short permanently attached catheter.

The methods, systems and devices described herein allow for the use of nearly any catheter with nearly any infusion device. Previously, catheters were often selected such that their burst pressure exceeded the theoretical limit of the pressure capable of being generated by the pumping mechanism of the infusion device. By selecting catheters in such a manner, the likelihood of catheter bursting due to pressure buildup following an occlusion could be minimized. However, in some instances, it may be desirable to use catheters that may burst at lower pressures. For example, such catheters may be softer (lower modulus), which may be more appropriate for use in delicate tissues such as brain parenchyma. Further, catheters with lower bursting pressures may be thinner, which would allow for a smaller diameter catheter introducer. Smaller diameter introducers may be desirable for use in delicate tissue. In some cases, catheters with lower bursting pressures are more compliant and can expand upon delivery of a pulse of fluid into a lumen. Thus, the release of the fluid from the catheter may be prolonged relative to a less compliant catheter. Regardless of the reason for selecting a catheter with a lower burst pressure, the present disclosure describes devices and methods for limiting the pressure within a catheter to reduce the likelihood of bursting. It will be understood that the methods, devices and systems described herein may be used regardless of the burst pressure of the catheter.

Figure 5:
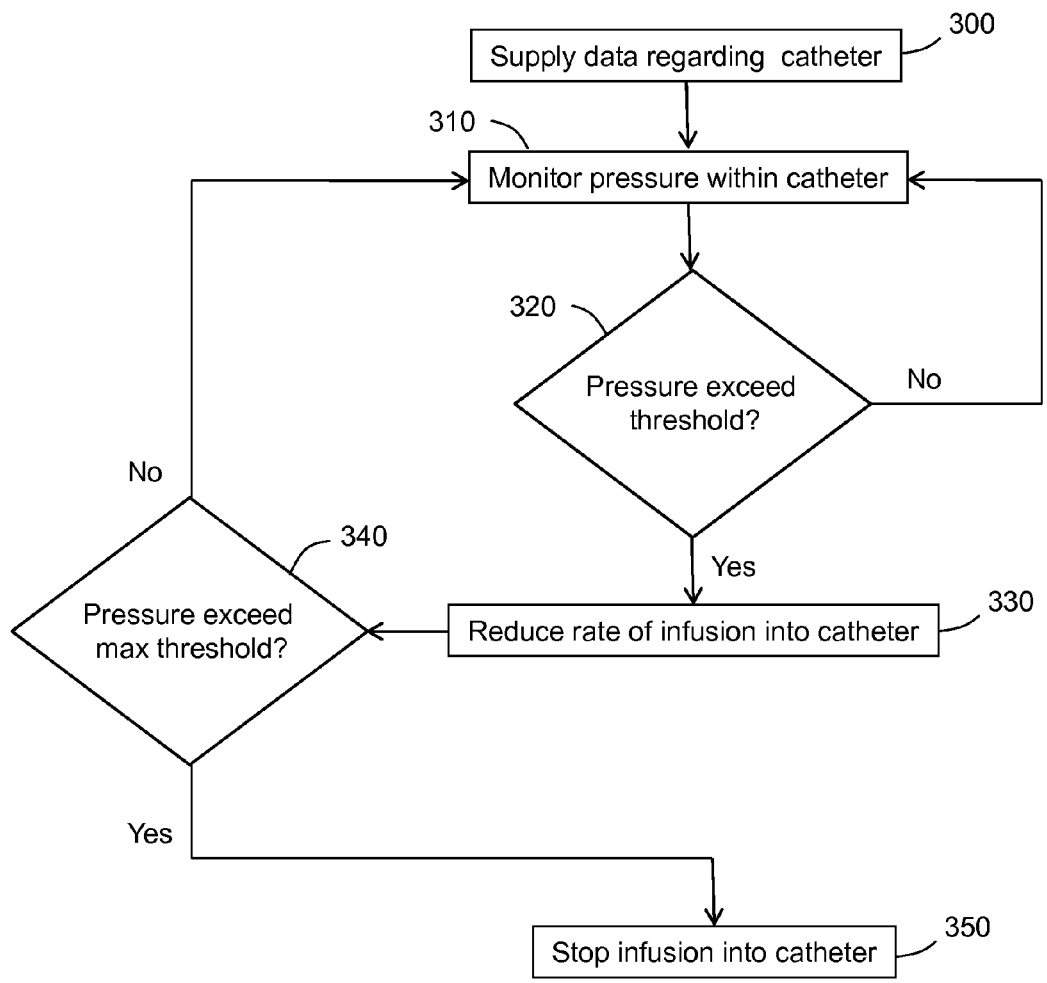
FIGS. 5-8 are flow diagrams illustrating overviews of embodiments of methods described herein.

By way of example and as a general overview, FIG. 5 illustrates a method for limiting pressure within a catheter. As shown in FIG. 5, the method includes supplying the implantable infusion device with data regarding the catheter (300). This data may include the maximum pressure within a lumen of the catheter that the catheter can withstand without bursting. In some embodiments, the supplied data includes the make and model of the catheter, and the implantable infusion device has relevant information regarding maximum pressure (or "burst" pressure) stored in memory, e.g. stored in a lookup table. It will be understood that the information regarding the maximum pressure that the catheter can withstand may be information that is at, for example, a cut off pressure that is 90% of maximum pressure or 85%, 80%, 75% or the like of the maximum pressure of the catheter. The cutoff pressure may be a pressure determined to reproducibly result in maintained catheter integrity (i.e., no bursting). Thus, the data supplied to the implantable medical device (or identified by the implantable device) does not necessarily include the value of the maximum pressure within the lumen of the catheter that the catheter can withstand before bursting—it may include data regarding some level of pressure less than the maximum pressure, such as a cutoff pressure.

Still with reference to FIG. 5, the method further includes monitoring pressure within the lumen of the catheter (310) and determining whether a threshold is exceeded (320). The threshold is based on the information regarding the catheter (300) and may be a pressure value below the maximal pressure or cutoff pressure. For example, the threshold may be 70%, 75%, 80%, 85%, 90%, 95%, or the like, below the cutoff pressure, which as discussed above, may be a value below the burst pressure. If the pressure is determined to not exceed the threshold (320), monitoring (310) continues. If the pressure is determined to exceed the threshold (320), the rate of infusion of fluid into the catheter from the implantable infusion device may be reduced (330). The reduction in infusion rate, may serve to decrease the pressure in the lumen of the catheter or slow the increase in pressure that results from an occlusion.

The method may also include detecting whether a maximum threshold is exceeded (340). The maximum threshold is a pressure value that, if reached, further infusion of fluid into the catheter (which may result in further pressure increases) is undesired, and infusion into the catheter is stopped (350). As discussed above, the maximum threshold may be the cutoff pressure. In many cases abrupt stopping of therapy is counter indicated due to withdrawal symptoms. However, in some situation cases, it may be more desirable to stop therapy than to have the catheter burst and deliver a large bolus of therapeutic agent to the patient. Further, as the rate of infusion may have been slowed (350) over time, abrupt withdrawal symptoms may not be experienced. In addition, if the catheter is completely occluded, no therapeutic agent is being delivered to the patient. Accordingly, cessation of therapy (350) should not result in additional withdrawal symptoms beyond those that may have already been experienced due to the occlusion.

The maximum threshold may be a value lower than the burst pressure, such as a cutoff pressure. In the embodiments depicted in FIG. 5, the maximum threshold is a pressure value higher than the initial threshold.

If it is determined that the maximum pressure threshold is not exceeded (340), further monitoring (310) and potential infusion rate reductions (330) may be continued. It will be understood that additional thresholds between the first and maximum thresholds may be employed and further reductions in rate of infusion may be made.

Figure 6:
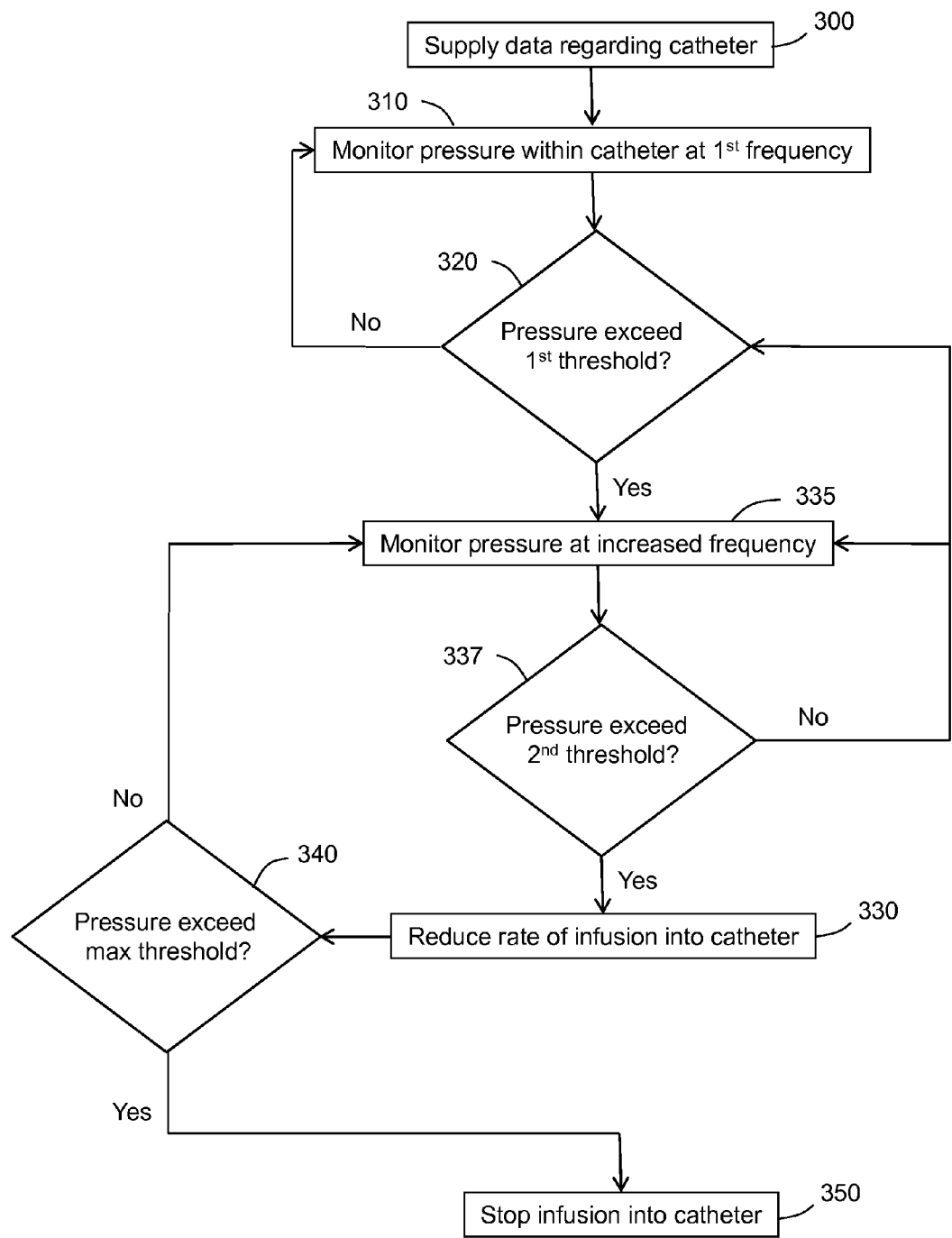

Referring now to FIG. 6, a method in which monitoring may occur in a more power efficient manner is described. In the depicted embodiment, data regarding the catheter is supplied to the implantable infusion device (300), e.g. as described above. Pressure within the lumen of the catheter is monitored with a low frequency of data acquisition from the pressure sensor circuitry (310). It will be understood that the frequency of data acquisition may depend on the system used. In some embodiments, a low frequency of data acquisition is acquisition of pressure data once a minute, once every five minutes, once every ten minutes, etc. In cases where the infusion system employs a piston pump, the data may be acquired once every two pump strokes, once every five pump strokes, once every ten pump strokes, etc., with faster pumping resulting in more frequent data acquisition (in terms of time) and slower pumping resulting in less frequent data acquisition.

Still with reference to FIG. 6, a determination is made as to whether the pressure exceeds a first low threshold value (320), which is based on the catheter employed. If the pressure in the lumen of the catheter exceeds the threshold (320), the pressure may be monitored at an increased frequency (335); e.g. by increasing frequency of pressure data acquisition. If a second threshold, which is higher than the first threshold, is exceeded (337), the rate of infusion of fluid into the catheter may be decreased (330). As discussed above with regard to FIG. 5, the reduction in infusion rate, may serve to decrease the pressure in the lumen of the catheter or slow the increase in pressure that results from an occlusion. If the second threshold is not exceeded (337), monitoring at the second frequency may continue (335) or a determination may again be made as to whether the first threshold is exceeded (320) to determine whether to monitor at the first (310) or second (335) frequency.

Still referring to FIG. 6, the method may also include detecting whether a maximum threshold is exceeded (340). If the maximum threshold is exceeded, infusion of therapeutic fluid into the catheter may be stopped (350) in some cases. It will be understood that the first, second and maximum pressures within the lumen of the catheter are based on the catheter being employed. It will also be understood that additional thresholds with further increases in the frequency of monitoring may be readily added to further enhance the power efficiency of monitoring, with increased monitoring (and thus power consumption) being performed as the pressure within the lumen approaches the maximum catheter pressure.

In some embodiments, it is desirable to monitor the rate at which therapeutic fluid is infused into the catheter. As the rate of infusion increases, the rate of increase in pressure within a catheter (if there is an occlusion) increases. Accordingly, it may be desirable to increase the frequency of pressure monitoring when the infusion rate is high. As a corollary, it may be desirable to decrease the rate of pressure monitoring when the rate of infusion is low so that power consumption may be reduced.

Figure 7:
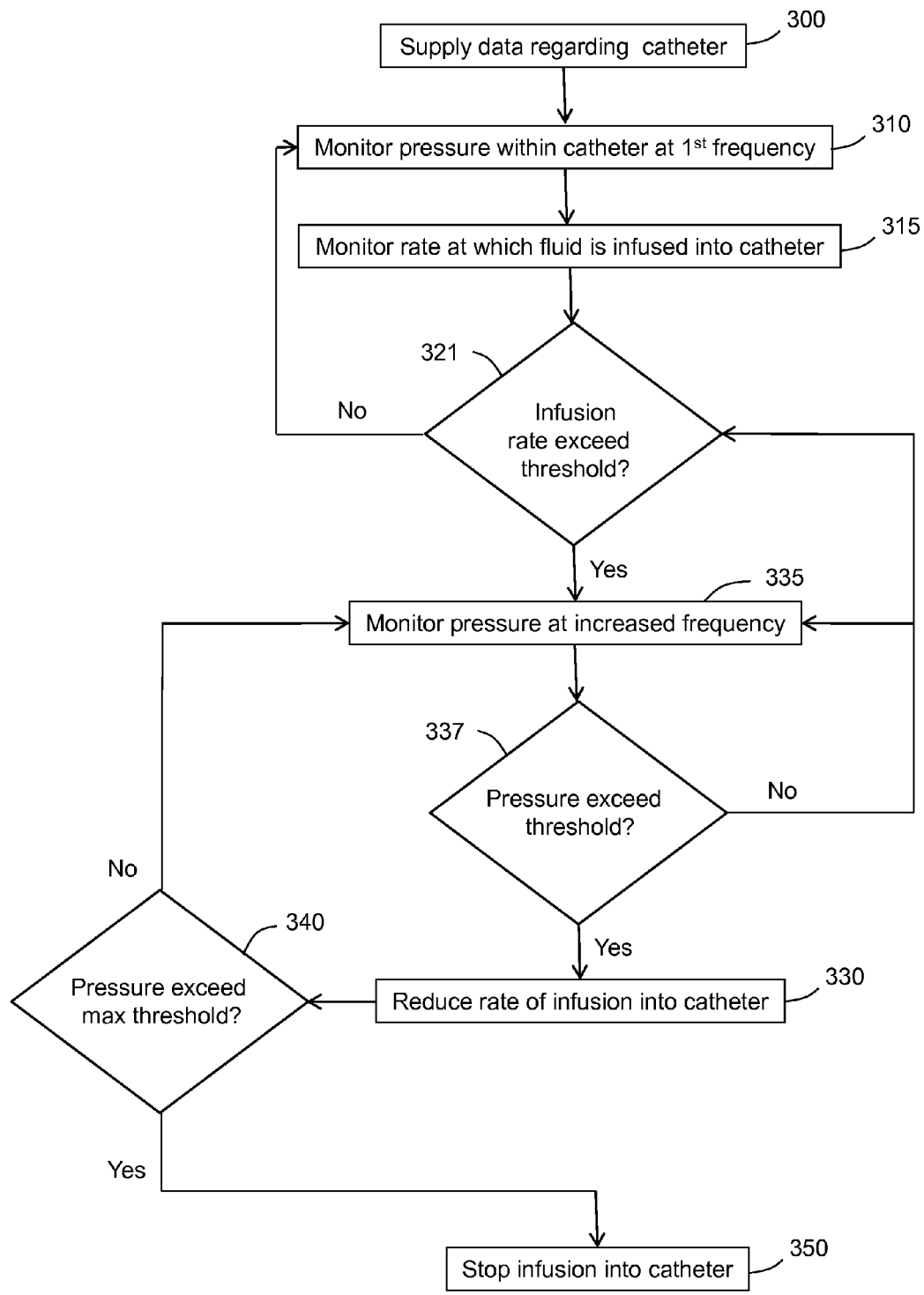

For example and with reference to FIG. 7, a method that changes the frequency of monitoring when the rate of infusion changes is shown. If, for example, monitoring at a basal infusion rate includes acquisition of pressure data every five minutes, the frequency of data acquisition during a period of increased infusion, such as with bolus delivery, may be increased.

As with the previously depicted methods, the method of FIG. 7 includes supplying the implantable infusion device with data regarding the catheter (300), e.g. as described above. The method further includes monitoring pressure in the lumen of the catheter at first lower frequency (310) and monitoring the rate at which fluid is infused into the catheter (315). The rate at which fluid is infused into the catheter may be monitored via any suitable manner. For example, the rate may be derived from instructions regarding the delivery rate programmed in memory, may be derived from monitoring of the pumping mechanism such as by counting strokes of a piston pump or rolls of a peristaltic pump that deliver known quantities of fluid per stroke or roll, flow rate sensors, duty cycle of a valve that controls flow (e.g., on/off) of a fluid configured to flow at a known rate, or the like. A determination may be made as to whether the infusion rate, or an indicator thereof, exceeds a predetermined threshold (321). If the infusion rate does not exceed the threshold (321), pressure monitoring may continue at the first frequency (310). If the infusion rate exceeds the first threshold (321), pressure may be monitored at an increased frequency (335) and a determination may be made as to whether the pressure exceeds a predetermined threshold (337) based on the catheter being used. If the pressure does not exceed the threshold (337), pressure may be monitored at the increased frequency (335) or a determination may be made as to whether the infusion rate threshold is exceeded (321) for determining whether to monitor pressure at the first (310) or second (335) frequency. If the pressure exceeds the threshold, the rate of infusion into the catheter may be reduced (330). In some cases, it may be desirable to determine whether a maximum pressure threshold is exceeded (340) and to stop infusion into the catheter (350), as discussed above with regard to FIGS. 5-6.

It will also be understood that, with regard to the methods discussed with regard to, or depicted in, FIGS. 5-7 above or FIG. 8 below, additional thresholds regarding the rate of infusion with further increases in the frequency of pressure monitoring may be readily added to further enhance the power efficiency of monitoring, with increased monitoring (and thus power consumption) being performed as the infusion rate increases. The tradeoff of power consumption for increased monitoring may be desired at high infusion rates because the rate at which the pressure increases may be rapid if the catheter is occluded. Accordingly, absent frequent pressure monitoring, an occlusion may not be detected until after a catheter has already reached or exceed its maximum pressure threshold.

It will also be understood that the frequency of pressure monitoring may be changed based on any combination of pressure thresholds and infusion rate thresholds. For example and with reference to FIG. 8, one such example is shown. In FIG. 8, 'A' and 'B' are used to link various points of exit from, and entry to, some of the depicted steps or blocks. For example, decision blocks 320 and 321 may flow to 'A', which means they may flow to enter block 310 as depicted. By way of further example, decision blocks 340 and 337 may flow to 'B', which means they may flow to decision blocks 320 or 321 as depicted.

Figure 8:
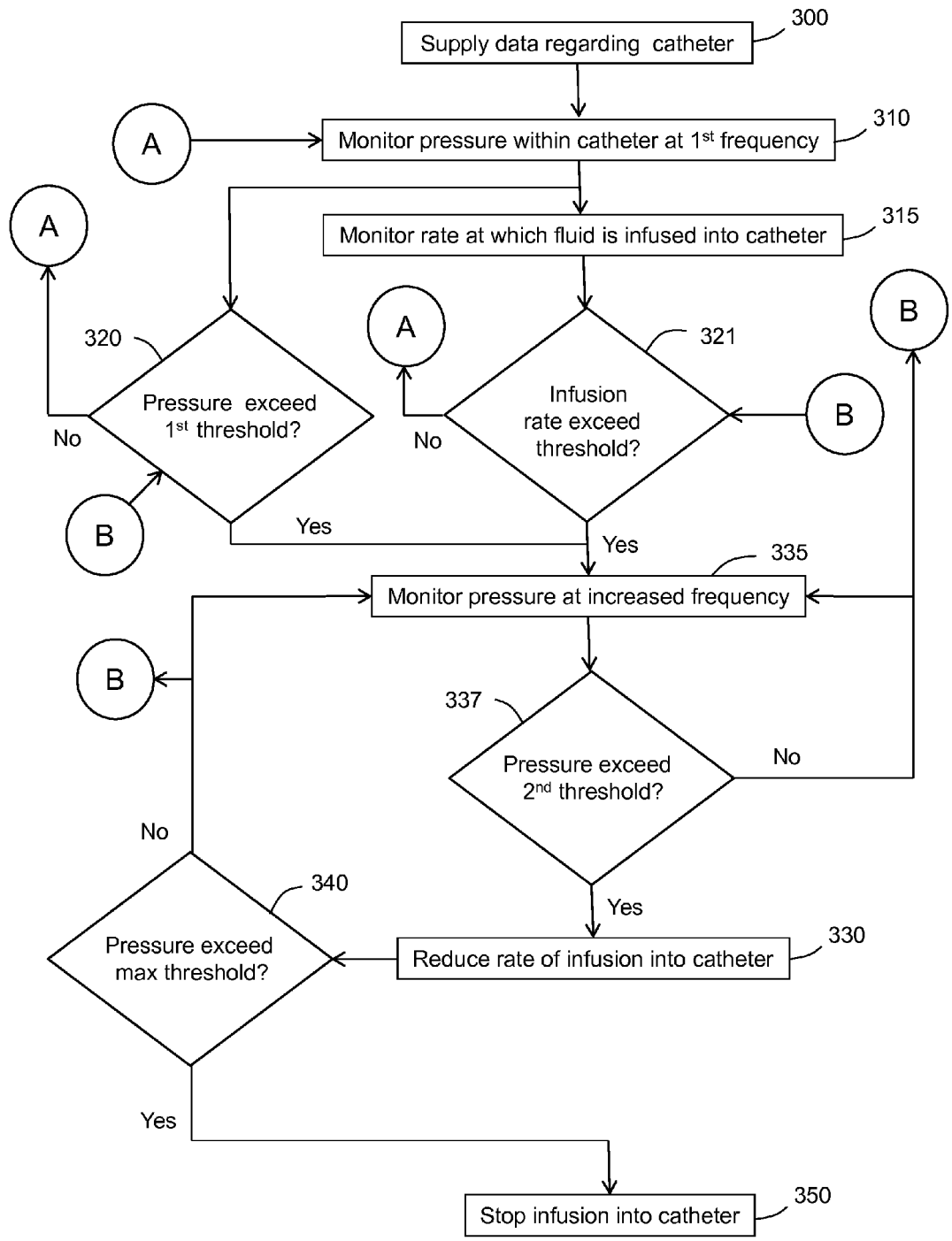

As with the other methods described herein, the method depicted in FIG. 8 includes supplying data regarding the catheter to the implantable infusion device (300). Pressure within the lumen of the catheter is initially monitored at a first low frequency (310) and the rate of infusion of fluid into the catheter is monitored (315). If the pressure is determined to not exceed the first threshold (320) and the rate of infusion does not exceed the threshold (321), the monitoring of pressure at the first frequency (310) continues. If the pressure exceeds a first threshold (320) or if the infusion rate exceeds a threshold (321), the pressure may be monitored at a second increased frequency (335). The second increased frequency of pressure monitoring (335) may be determined based on the detected pressure (310) and the rate of the infusion (315). The control electronics of the implantable infusion device (e.g. processor and memory) may contain a lookup table including cells regarding pressure, rate of infusion and rate of pressure monitoring for the catheter being used or may calculate the frequency of pressure monitoring as a function of monitored pressure and infusion rate based on the catheter being used. In any case, if pressure is determined not to exceed a second threshold (337), which is higher than the first threshold, the pressure may continue to be monitored at the second increased frequency (335). Alternatively, it may be desirable to determine whether the pressure exceeds the first lower threshold (320) and the infusion rate threshold (321) to determine whether to monitor pressure at the first (310) or second (335) frequency.

If pressure is determined to exceed the second threshold (337), the rate at which fluid is infused into the lumen of the catheter may be reduced (330), and a determination may be made as to whether a maximum pressure threshold for the catheter is exceeded (340). If the maximum pressure is exceeded, infusion of fluid into the catheter may be stopped (350) in some cases. If the maximum pressure is determined to not be exceeded (340), the pressure may continue to be monitored at the second increased frequency (335). Alternatively, it may be desirable to determine whether the pressure exceeds the first lower threshold (320) and the infusion rate threshold (321) to determine whether to monitor pressure at the first (310) or second (335) frequency.

It will be understood that FIG. 8 shows only one example of how the frequency of pressure monitoring may be changed based on any suitable combination of pressure thresholds and infusion rate thresholds and that other processes are contemplated herein. For example, the determinations with regard to the first threshold (320) and the infusion rate (321) are shown as being in parallel in FIG. 8. Of course, it will be understood that these determinations may be made in series or sequentially.

It will be also understood that FIGS. 5-8 are presented for purposes of illustration and not limitation and that the various steps presented in any of FIGS. 5-8 may be interchanged, substituted, combined or omitted, as appropriate. Process steps other than those described herein, or derivations of the steps or components to carry out the steps, may be employed.

Figure 9:
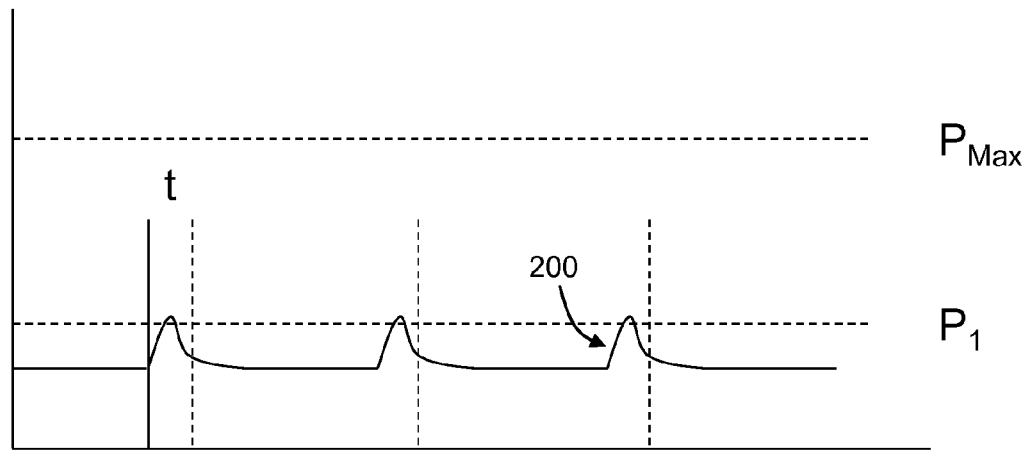
FIGS. 9-11 are schematic plots of pressure within a lumen of a catheter over time, for purposes of illustrating various concepts described herein.
Figure 10:
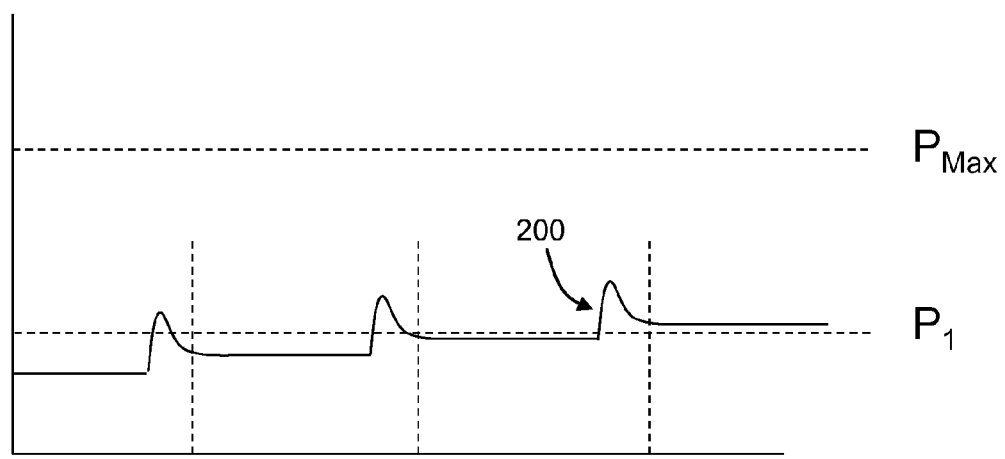
Figure 11:
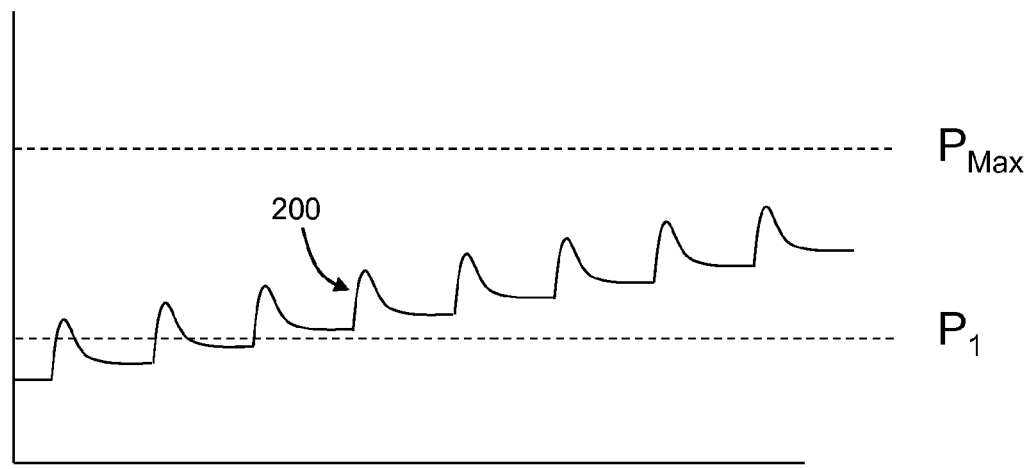

Referring now to FIGS. 9-11 schematic plots of pressure within a lumen of a catheter versus time are shown for purposes of illustration. FIG. 9 is a plot representative of a properly function, non-occluded catheter, which shows periodic or intermittent pressure spikes 200 due to pulses of fluid being delivered from a reservoir of an infusion device into the lumen of the catheter. Such spikes 200 may be observed with infusion devices having pumping mechanisms that are capable of delivering small pulses or boluses of fluid, such as peristaltic pumps, piston pumps, or the like. The pressure pulses 200 associated with puslatile fluid delivery have characteristic pressure decay profiles.

As shown in FIG. 9, the peak of the pressure spikes 200 may cross a pressure threshold ($P_1$, shown by dashed horizontal line), which as indicated in the methods depicted in FIGS. 5-8 above may result in increased frequency of pressure monitoring. However, the plot depicted in FIG. 9 is representative of a properly functioning catheter with no occlusions. Accordingly, increased frequency of monitoring is such a situation would be undesirable as it may result in increased power consumption. Accordingly, it may be desirable to set the pressure threshold ($P_1$) higher or to monitor pressure at a fixed time relative to delivery of a pulse of fluid into the catheter. For example, the solid horizontal line depicted in FIG. 9 represents the time at which a pulse or bolus begins and the dashed horizontal lines represent a time (t) following the beginning of a pulse when pressure may be monitored. Any suitable time following the beginning of a pulse (e.g., following completion of a stroke of a piston or roll of a peristaltic pump) may be used. In some embodiments, the pumping mechanism is a piston pump and the pressure is monitored (e.g., pressure data is acquired) between 30 and 100 milliseconds following a piston stroke. By monitoring at a fixed time following a pulse, changes in pressure due to an occlusion may be more reproducibly detected.

For example and with reference to FIG. 10, a schematic plot of pressure versus time is shown in which the catheter is at least partially occluded is shown. With each subsequent pulse 200, the baseline pressure rises. While the peak of the first pulse 200 is above the pressure threshold ($P_1$), as with the peaks shown in FIG. 9, the baseline, or a portion of the pulse pressure profile in the tail of the decay, is also above the pressure threshold ($P_1$) following the third pulse depicted in FIG. 10. The situation depicted in FIG. 10, unlike the situation depicted in FIG. 9, is a situation that may warrant increased frequency of pressure monitoring, as the catheter is at least partially occluded.

By way of further example, FIG. 11 depicts a schematic plot of pressure in a lumen of a catheter versus time in an occluded catheter in which the rate of infusion is higher than that shown in FIGS. 9-10. By comparing, for example, FIG. 10 to FIG. 11, it can be seen that, at higher infusion rates, the pressure in the lumen of an occluded catheter may rise more quickly than at lower rates of infusion. Accordingly, the pressure within the lumen of the catheter may approach the maximum pressure ($P_{Max}$) of the catheter more rapidly. In such situations, increased frequency of pressure monitoring, such as depicted and described above with regard to FIGS. 7-8, may be desirable.

In many of the embodiments depicted and described above, the infusion device controls the rate of infusion (i.e., decreases the rate of infusion) if certain pressure thresholds are exceeded, are exceed for predetermined period of time, or the like. In many embodiments, it may also be desirable to provide an alert to a patient in situations that warrant such a reduction in infusion rate. The alert may be in the form of an audible cue, a tactile cue such as vibration, or the like. This alert can prompt the patient to seek medical attention. In embodiments, the infusion device is configured to send an alert to a healthcare provider via the internet, a telephone network or the like. Alert subroutines or sub-processes may be incorporated into the methods depicted and described above or may be processes of their own. Other actions may also or alternatively be taken in response to detection of thresholds, or the like.

Figure 12:
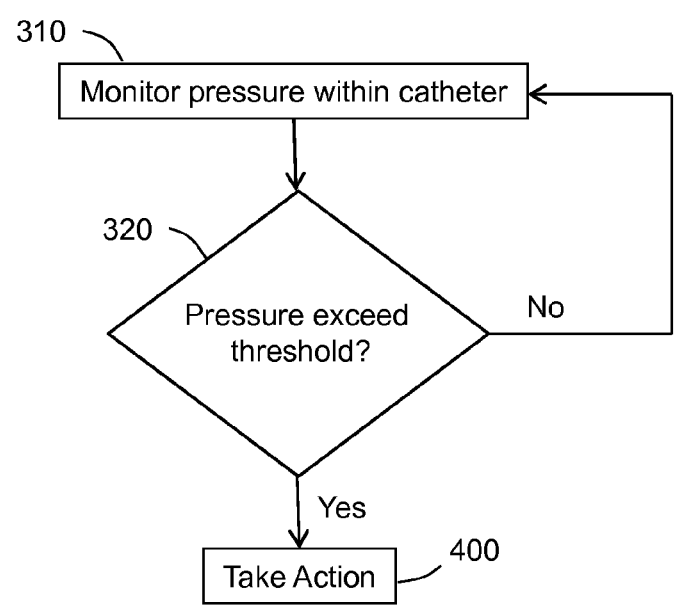
FIGS. 12-16 are flow diagrams illustrating overviews of embodiments of methods described herein.
Figure 13:
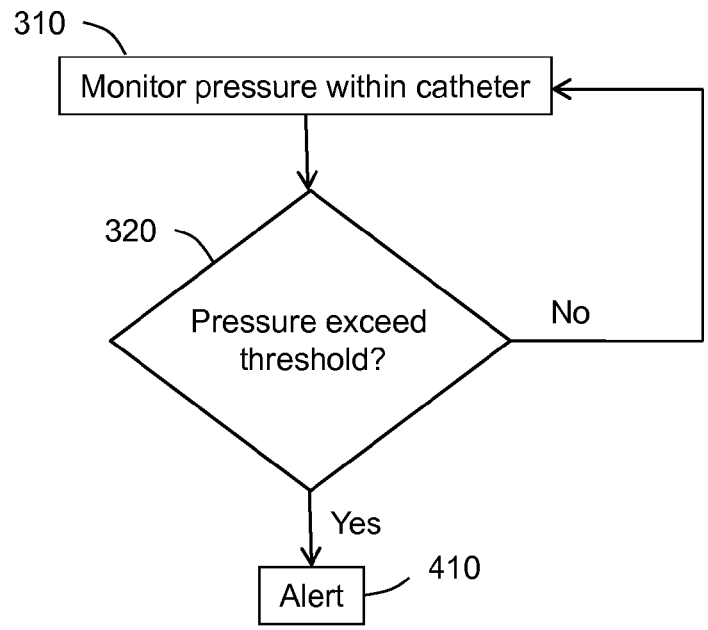
Figure 14:
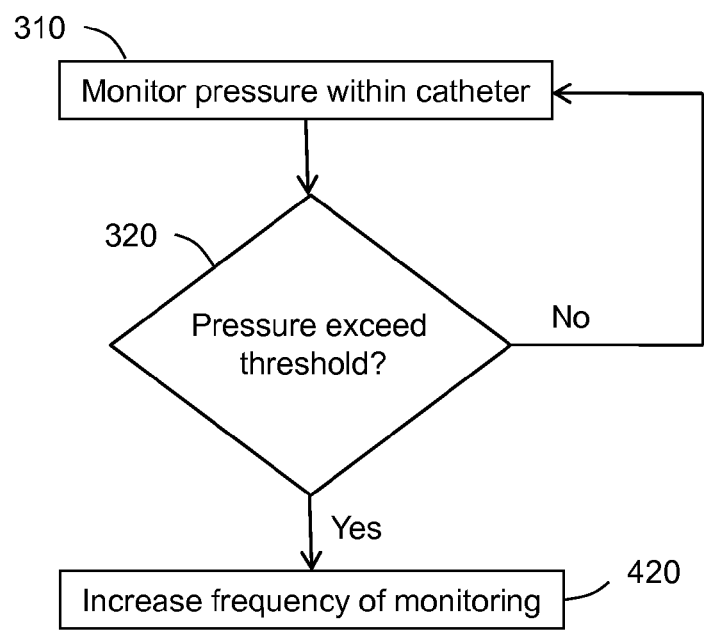
Figure 15:
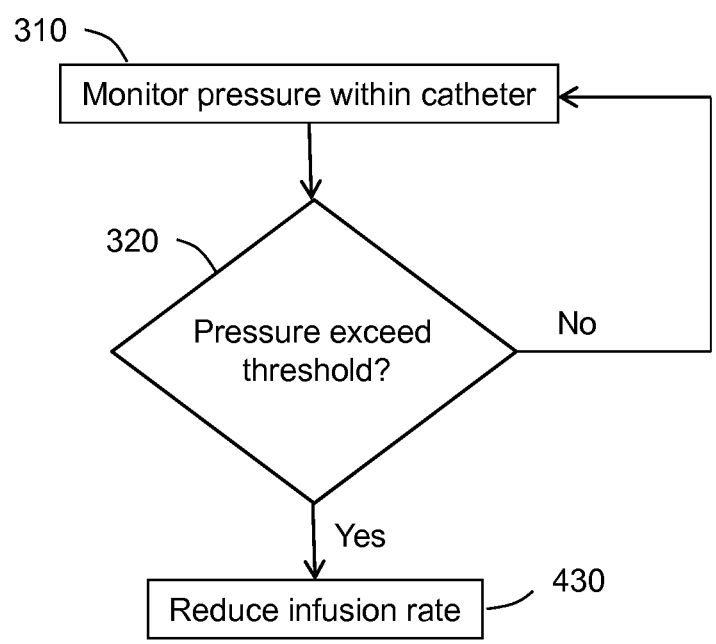

For example and with reference to FIG. 12, a method may include monitoring pressure within a catheter 310, determining whether the pressure exceeds a threshold 320, and taking action (400) if the pressure exceeds a threshold. Any suitable action may be taken. By way of example, FIG. 13 depicts a method where an alert is provided (410) if monitored pressure (310) is determined (320) to exceed a threshold; FIG. 14 depicts a method where frequency of pressure monitoring is increased (420) if monitored pressure (310) is determined (320) to exceed a threshold; and FIG. 15 depicts a method where infusion rate is reduced (430) if monitored pressure (310) is determined (320) to exceed a threshold. It will be understood that more than one threshold may be included in the methods depicted in FIGS. 13-15; one or more of the steps depicted in any one of FIGS. 13-15 may be combined, substituted, or interchanged with steps depicted in another of FIGS. 13-15; and that any steps depicted in FIGS. 13-15 may be included into the methods depicted and described above with regard to FIGS. 5-8; alone or in combination, in any suitable manner.

Figure 16:
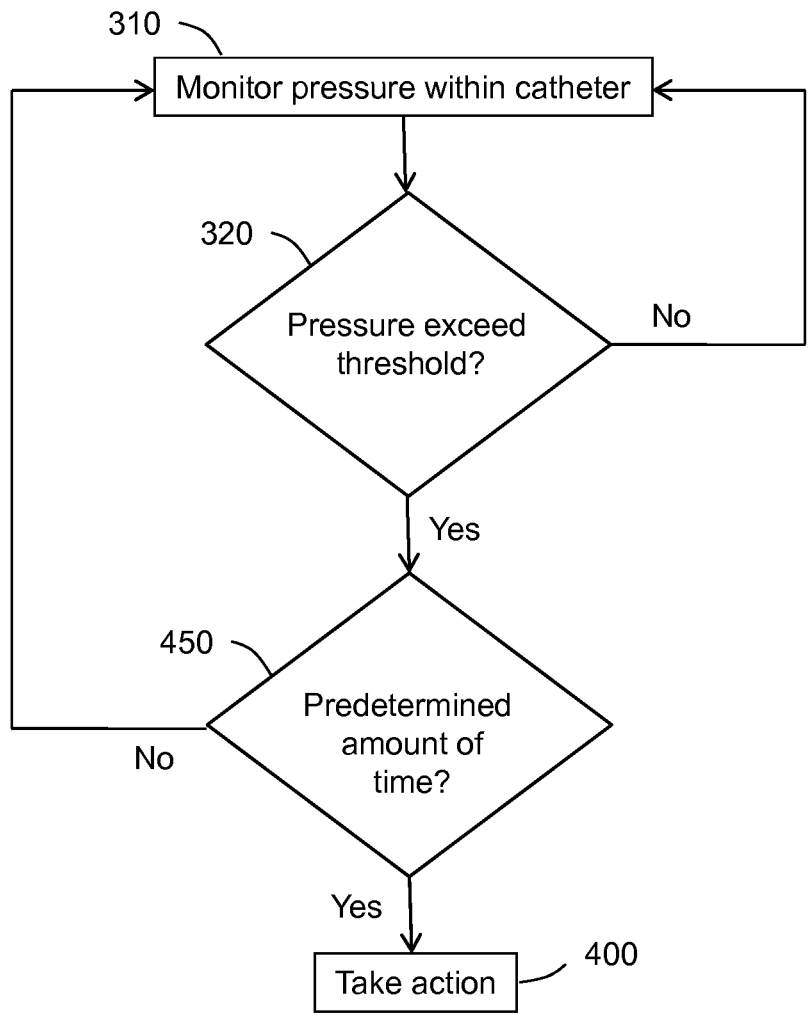

Referring now to FIG. 16, an embodiment of a method in which action is taken (400) after a pressure threshold is determined (320) to have been exceeded for a predetermined amount of time (450). The method depicted in FIG. 16 may be incorporated, in whole or in part, with or without additional threshold value determinations, into any of the methods described herein, including the methods depicted in and described with regard to FIGS. 5-8 and 13-15.

In embodiments, pressure data is stored in memory of the infusion device as it is collected and may be transmitted to an external device during a patient visit to the clinic, may be transmitted over the internet to a healthcare provider, or the like.

It will be understood that infusion devices and systems configured to carry out the methods described herein are contemplated. It will be further understood that computer readable media that, when executed, cause an implantable infusion device or system to carry out the methods described herein are contemplated. The computer readable media may be non-transitory (i.e., existing in a tangible form for more than a fleeting instant or seconds) such as stored in memory.

Overview of Various Aspects

The present disclosure describes various embodiments of methods, systems, devices and the like for use in monitoring pressure in a lumen of a catheter of an implantable infusion system. The methods described herein, in many embodiments, are particularly relevant for monitoring catheter occlusions and taking appropriate action when the catheter is occluded (partially or fully, as the case may be).

In a first aspect, a method carried out by an implantable infusion device includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate and monitoring pressure via a pressure sensor in communication with the lumen of the catheter. Monitoring the pressure includes acquiring pressure data from the pressure sensor at a first frequency. The method also includes (i) determining whether the monitored pressure exceeds a first threshold, wherein the first threshold is based on the data regarding the catheter; and (ii) decreasing the rate at which the fluid is delivered from the reservoir into the catheter if the monitored pressure is determined to exceed the threshold.

A second aspect is a method of the first aspect, further including (i) determining whether the monitored pressure exceeds a second threshold, wherein the second threshold is indicative of a lower pressure than the first threshold; and (ii) increasing the frequency of acquisition of pressure data from the pressure sensor if the monitored pressure is determined to exceed the second threshold.

A third aspect is a method of the first or second aspect, further comprising (i) determining whether the monitored pressure exceeds a third threshold, wherein the third threshold is indicative of a higher pressure than the first threshold; and (i) stopping the infusion from the reservoir into the lumen of the catheter if the pressure is determined to exceed the third threshold.

A fourth aspect is a method of any of the first three aspects, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

A fifth aspect is a method of any of the first four aspect, further comprising (i) monitoring a rate of infusion of fluid from the reservoir into the lumen of the catheter; (ii) determining whether the rate of infusion exceeds a threshold; and (iii) increasing the frequency of the monitoring of pressure if the rate of infusion is determined to exceed the threshold.

A sixth aspect is a method of any of the first five aspects, further comprising monitoring a rate of infusion of fluid from the reservoir into the lumen of the catheter, wherein the first pressure threshold is further based on the monitored rate of infusion.

A seventh aspect is an implantable infusion device comprising (i) a reservoir for containing a fluid; (ii) a pumping mechanism operably coupled to the reservoir and configured to drive fluid from the reservoir into a lumen of a catheter when the catheter is operably coupled to the infusion device; (iii) a pressure sensor configured to be in communication with the lumen of the catheter when the catheter is operably coupled to the infusion device; and (iv) control electronics operably coupled to the pumping mechanism and the pressure sensor and configured to control the pumping mechanism based on the sensed pressure, wherein the control electronics are further configured to carry out a method according to any of the first six aspects.

An eighth aspect is a non-transitory computer readable medium containing instructions that, when implemented by an implantable infusion device, cause the infusion device to carry out the method according to any of the first six aspects.

A ninth aspect is an implantable infusion device comprising the non-transitory computer readable medium of the eighth aspect.

A tenth aspect is a method carried out by an implantable infusion device. The method includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate, and monitoring pressure via a pressure sensor in communication with the lumen of the catheter. Monitoring the pressure includes acquiring pressure data from the pressure sensor at a first frequency. The method also includes determining whether the monitored pressure exceeds a first threshold. The first threshold is based on the data regarding the catheter. The method additionally includes (i) monitoring a rate of infusion of fluid from the reservoir into the lumen of the catheter; (ii) determining whether the rate of infusion exceeds a threshold rate of infusion; and (iii) increasing the frequency of acquisition of pressure data from the pressure sensor if the monitored pressure is determined to exceed the first threshold or if the monitored rate of infusion is determined to exceed the threshold rate of infusion.

An eleventh aspect is a method of the tenth aspect, further comprising determining whether the monitored pressure exceeds a second threshold, wherein the second threshold is indicative of a higher pressure than the first threshold; and decreasing the rate at which the fluid is delivered from the reservoir into the catheter if the monitored pressure is determined to exceed the second threshold.

A twelfth aspect is a method of the tenth or eleventh aspect, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

A thirteenth aspect is an implantable infusion device comprising: (i) a reservoir for containing a fluid; (ii) a pumping mechanism operably coupled to the reservoir and configured to drive fluid from the reservoir into a lumen of a catheter when the catheter is operably coupled to the infusion device; (iii) a pressure sensor configured to be in communication with the lumen of the catheter when the catheter is operably coupled to the infusion device; and (iv) control electronics operably coupled to the pumping mechanism and the pressure sensor and configured to control the pumping mechanism based on the sensed pressure, wherein the control electronics are further configured to carry out the method of any of the tenth, eleventh, or twelfth aspects.

A fourteenth aspect is a non-transitory computer readable medium containing instructions that, when implemented by an implantable infusion device, cause the infusion device to carry out a method of any of the tenth, eleventh, or twelfth aspects.

A fifteenth aspect is an implantable infusion device comprising the non-transitory computer readable medium of the fourteenth aspect.

A sixteenth aspect is a method carried out by an implantable infusion device. The method includes receiving data regarding a catheter being used with the infusion device. The catheter has a lumen operably coupled to a reservoir of the infusion device and is configured to deliver fluid from the infusion device to a target location of a patient. The method further includes infusing fluid from the reservoir into the lumen of the catheter at a first rate and monitoring pressure via a pressure sensor in communication with the lumen of the catheter. Monitoring the pressure includes acquiring pressure data from the pressure sensor at a first frequency. The method also includes (i) monitoring a rate of infusion of fluid from the reservoir into the lumen of the catheter; (ii) deriving a threshold pressure based on the data regarding the catheter and the monitored rate of infusion; (iii) determining whether the pressure exceeds the threshold; and (iv) increasing the frequency of acquisition of pressure data from the pressure sensor if the monitored pressure is determined to exceed the threshold.

A seventeenth aspect is a method of the sixteenth aspect, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

An eighteenth aspect is an implantable infusion device comprising: (i) a reservoir for containing a fluid; (ii) a pumping mechanism operably coupled to the reservoir and configured to drive fluid from the reservoir into a lumen of a catheter when the catheter is operably coupled to the infusion device; (iii) a pressure sensor configured to be in communication with the lumen of the catheter when the catheter is operably coupled to the infusion device; and (iv) control electronics operably coupled to the pumping mechanism and the pressure sensor and configured to control the pumping mechanism based on the sensed pressure, wherein the control electronics are further configured to carry out the method of the sixteenth or seventeenth aspects.

A nineteenth aspect is a non-transitory computer readable medium containing instructions that, when implemented by an implantable infusion device, cause the infusion device to carry out the method according to the sixteenth or seventeenth aspects.

A twentieth aspect is an implantable infusion device comprising the non-transitory computer readable medium of the nineteenth aspect.

A twenty-first aspect is a method carried out by an implantable infusion device, comprising: (i) receiving data regarding a catheter being used with the infusion device, the catheter having a lumen operably coupled to a reservoir of the infusion device and configured to deliver fluid from the infusion device to a target location of a patient; (ii) infusing fluid from the reservoir into the lumen of the catheter at a first rate; (iii) monitoring pressure via a pressure sensor in communication with the lumen of the catheter, wherein monitoring the pressure comprises acquiring pressure data from the pressure sensor at a first frequency; (iv) determining whether the monitored pressure exceeds a first threshold, wherein the first threshold is based on the data regarding the catheter; and (v) increasing the frequency of acquisition of pressure data from the pressure sensor if the monitored pressure is determined to exceed the first threshold.

A twenty-second aspect is a method carried out by an implantable infusion device, comprising: (i) monitoring pressure via a pressure sensor in communication with the lumen of a catheter, wherein monitoring the pressure comprises acquiring pressure data from the pressure sensor at a first frequency; (ii) determining whether the monitored pressure exceeds a threshold; and (iii) increasing the frequency of acquisition of pressure data from the pressure sensor if the monitored pressure is determined to exceed the threshold.

A twenty-third aspect is a method carried out by an implantable infusion device comprising: (i) infusing fluid from a reservoir into a lumen of a catheter at a first rate; (ii) monitoring pressure via a pressure sensor in communication with the lumen of the catheter, wherein monitoring the pressure comprises acquiring pressure data from the pressure sensor at a first frequency; (iii) determining whether the monitored pressure exceeds a first threshold; (iv) monitoring a rate of infusion of fluid from the reservoir into the lumen of the catheter; (v) determining whether the rate of infusion exceeds a threshold rate of infusion; and (vi) increasing the frequency of acquisition of pressure data from the pressure sensor if the monitored pressure is determined to exceed the first threshold or if the monitored rate of infusion is determined to exceed the threshold rate of infusion.

A twenty-fourth aspect is a method carried out by an implantable infusion device comprising: (i) infusing fluid from a reservoir into a lumen of a catheter at a first rate; (ii) monitoring pressure via a pressure sensor in communication with the lumen of the catheter, wherein monitoring the pressure comprises acquiring pressure data from the pressure sensor at a first frequency; (iii) monitoring a rate of infusion of fluid from the reservoir into the lumen of the catheter; (iv) determining whether the rate of infusion exceeds a threshold rate of infusion; and (v) increasing the frequency of acquisition of pressure data from the pressure sensor if the monitored rate of infusion is determined to exceed the threshold rate of infusion.

An twenty-fifth aspect is a non-transitory computer readable medium containing instructions that, when implemented by an implantable infusion device, cause the infusion device to carry out the method according to any of aspects 21-24.

A twenty-sixth aspect is an implantable infusion device comprising the non-transitory computer readable medium of the twenty-fifth aspect Those skilled in the art will recognize that the preferred embodiments may be altered or amended without departing from the true spirit and scope of the disclosure, as defined in the accompanying claims.

In the claims that follow, the designators "first", "second", "third" and the like are used for purposes of distinguishing between elements and not for purposes of enumerating the elements. For example, a "third" threshold does not necessarily imply that there are three thresholds but rather that the "third" threshold is distinct from the "first" threshold.

What is claimed is:

1. A method carried out by an implantable infusion device, comprising:
    receiving data regarding a catheter being used with the infusion device, wherein the data comprises information indicative of a burst pressure or a cutoff pressure of the catheter, the catheter having a lumen operably coupled to a reservoir of the infusion device and configured to deliver fluid from the infusion device to a target location of a patient;
    infusing fluid from the reservoir into the lumen of the catheter at a first rate;
    monitoring pressure via a pressure sensor in communication with the lumen of the catheter, wherein monitoring the pressure comprises acquiring pressure data from the pressure sensor at a first frequency;
    determining whether the monitored pressure exceeds a first threshold, wherein the first threshold is based on the data regarding the catheter; and
    decreasing the rate at which the fluid is delivered from the reservoir into the catheter if the monitored pressure is determined to exceed the threshold.

2. The method of claim 1, further comprising
    determining whether the monitored pressure exceeds a second threshold, wherein the second threshold is indicative of a lower pressure than the first threshold; and
    increasing the frequency of acquisition of pressure data from the pressure sensor if the monitored pressure is determined to exceed the second threshold.

3. The method of claim 1, further comprising
    determining whether the monitored pressure exceeds a third threshold, wherein the third threshold is indicative of a higher pressure than the first threshold; and
    stopping the infusion from the reservoir into the lumen of the catheter if the pressure is determined to exceed the third threshold.

4. The method of claim 1, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

5. The method of claim 1, further comprising
    monitoring a rate of infusion of fluid from the reservoir into the lumen of the catheter;
    determining whether the rate of infusion exceeds a threshold; and
    increasing the frequency of the monitoring of pressure if the rate of infusion is determined to exceed the threshold.

6. The method of claim 1, further comprising monitoring a rate of infusion of fluid from the reservoir into the lumen of the catheter, wherein the first pressure threshold is further based on the monitored rate of infusion.

7. An implantable infusion device comprising:
    a reservoir for containing a fluid;

a pumping mechanism operably coupled to the reservoir and configured to drive fluid from the reservoir into a lumen of a catheter when the catheter is operably coupled to the infusion device;

a pressure sensor configured to be in communication with the lumen of the catheter when the catheter is operably coupled to the infusion device; and control electronics operably coupled to the pumping mechanism and the pressure sensor and configured to control the pumping mechanism based on the sensed pressure, wherein the control electronics are further configured to carry out the method of claim 1.

8. A non-transitory computer readable medium containing instructions that, when implemented by an implantable infusion device, cause the infusion device to carry out the method according to claim 1.

9. An implantable infusion device comprising the non-transitory computer readable medium of claim 8.

10. A method carried out by an implantable infusion device comprising:

receiving data regarding a catheter being used with the infusion device, wherein the data comprises information indicative of a burst pressure or a cutoff pressure of the catheter, the catheter having a lumen operably coupled to a reservoir of the infusion device and configured to deliver fluid from the infusion device to a target location of a patient;

infusing fluid from the reservoir into the lumen of the catheter at a first rate;

monitoring pressure via a pressure sensor in communication with the lumen of the catheter, wherein monitoring the pressure comprises acquiring pressure data from the pressure sensor at a first frequency;

determining whether the monitored pressure exceeds a first threshold, wherein the first threshold is based on the data regarding the catheter;

monitoring a rate of infusion of fluid from the reservoir into the lumen of the catheter;

determining whether the rate of infusion exceeds a threshold rate of infusion; and increasing the frequency of acquisition of pressure data from the pressure sensor if the monitored pressure is determined to exceed the first threshold or if the monitored rate of infusion is determined to exceed the threshold rate of infusion.

11. The method of claim 10, further comprising determining whether the monitored pressure exceeds a second threshold, wherein the second threshold is indicative of a higher pressure than the first threshold; and decreasing the rate at which the fluid is delivered from the reservoir into the catheter if the monitored pressure is determined to exceed the second threshold.

12. The method of claim 10, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

13. An implantable infusion device comprising:

a reservoir for containing a fluid;

a pumping mechanism operably coupled to the reservoir and configured to drive fluid from the reservoir into a lumen of a catheter when the catheter is operably coupled to the infusion device;

a pressure sensor configured to be in communication with the lumen of the catheter when the catheter is operably coupled to the infusion device; and control electronics operably coupled to the pumping mechanism and the pressure sensor and configured to control the pumping mechanism based on the sensed pressure, wherein the control electronics are further configured to carry out the method of claim 10.

14. A non-transitory computer readable medium containing instructions that, when implemented by an implantable infusion device, cause the infusion device to carry out the method according to claim 10.

15. An implantable infusion device comprising the non-transitory computer readable medium of claim 14.

16. A method carried out by an implantable infusion device comprising:

receiving data regarding a catheter being used with the infusion device, wherein the data comprises information regarding a burst pressure or a cutoff pressure of the catheter, the catheter having a lumen operably coupled to a reservoir of the infusion device and configured to deliver fluid from the infusion device to a target location of a patient;

infusing fluid from the reservoir into the lumen of the catheter at a first rate;

monitoring pressure via a pressure sensor in communication with the lumen of the catheter, wherein monitoring the pressure comprises acquiring pressure data from the pressure sensor at a first frequency;

monitoring a rate of infusion of fluid from the reservoir into the lumen of the catheter;

deriving a threshold pressure based on the data regarding the catheter and the monitored rate of infusion;

determining whether the pressure exceeds the threshold; and increasing the frequency of acquisition of pressure data from the pressure sensor if the monitored pressure is determined to exceed the threshold.

17. The method of claim 16, wherein infusing fluid from the reservoir into the lumen of the catheter comprises delivering a pulse of fluid, and wherein monitoring pressure comprises acquiring pressure data from the pressure sensor at a predetermined amount of time following delivery of the pulse of fluid.

18. An implantable infusion device comprising:

a reservoir for containing a fluid;

a pumping mechanism operably coupled to the reservoir and configured to drive fluid from the reservoir into a lumen of a catheter when the catheter is operably coupled to the infusion device;

a pressure sensor configured to be in communication with the lumen of the catheter when the catheter is operably coupled to the infusion device; and control electronics operably coupled to the pumping mechanism and the pressure sensor and configured to control the pumping mechanism based on the sensed pressure, wherein the control electronics are further configured to carry out the method of claim 16.

19. A non-transitory computer readable medium containing instructions that, when implemented by an implantable infusion device, cause the infusion device to carry out the method according to claim 16.

20. An implantable infusion device comprising the non-transitory computer readable medium of claim 19.

21. A method carried out by an implantable infusion device, comprising:

receiving data regarding a catheter being used with the infusion device, wherein the data comprises information indicative of a burst pressure or a cutoff pressure of the catheter, the catheter having a lumen operably coupled to a reservoir of the infusion device and configured to deliver fluid from the infusion device to a target location of a patient;

infusing fluid from the reservoir into the lumen of the catheter at a first rate;

monitoring pressure via a pressure sensor in communication with the lumen of the catheter, wherein monitoring the pressure comprises acquiring pressure data from the pressure sensor at a first frequency;

determining whether the monitored pressure exceeds a first threshold, wherein the first threshold is based on the data regarding the catheter; and increasing the frequency of acquisition of pressure data from the pressure sensor if the monitored pressure is determined to exceed the first threshold.

* * * * *